United States Patent
Neeman et al.

(10) Patent No.: US 9,492,100 B2
(45) Date of Patent: Nov. 15, 2016

(54) MAGNETIC RESONANCE IMAGING FOR DETECTING CARDIAC DISEASES

(71) Applicant: YEDA RESEARCH AND DEVELOPMENT CO. LTD., Rehovot (IL)

(72) Inventors: Michal Neeman, Mazkeret Batya (IL); Moriel Vandsburger, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 127 days.

(21) Appl. No.: 14/242,965

(22) Filed: Apr. 2, 2014

(65) Prior Publication Data
US 2014/0303479 A1    Oct. 9, 2014

Related U.S. Application Data

(60) Provisional application No. 61/807,791, filed on Apr. 3, 2013.

(51) Int. Cl.
*A61B 5/055* (2006.01)
*G01R 33/56* (2006.01)
*A61B 5/00* (2006.01)

(52) U.S. Cl.
CPC ............. *A61B 5/055* (2013.01); *A61B 5/0044* (2013.01); *G01R 33/5605* (2013.01); *A61B 2576/023* (2013.01)

(58) Field of Classification Search
CPC .......... A61B 2576/023; A61B 5/0044; A61B 5/055; G01R 33/5605
See application file for complete search history.

(56) References Cited

U.S. PATENT DOCUMENTS

2002/0188190 A1   12/2002   Kassai et al.
2004/0059213 A1   3/2004    Kassai et al.

OTHER PUBLICATIONS

Amado et al.; "Accurate and objective infarct sizing by contrast-enhanced magnetic resonance imaging in a canine myocardial infarction model", 2004; 44(12): 2383-2389.

Arenal et al.; "Do the spatial characteristics of myocardial scar tissue determine the risk of ventricular arrhythmias?", Cardiovascular Research, 2012; 94(2): 324-332.

Babu-Narayan et al.; "Ventricular fibrosis suggested by cardiovascular magnetic resonance in adults with repaired tetralogy of fallot and its relationship to adverse markers of clinical outcome", Circulation, 2006; 113(3): 405-413.

Bernstein et al.; "Nephrogenic systemic fibrosis: A systemic fibrosing disease resulting from gadolinium exposure", Best practice & research. Clinical rheumatology, 2012; 26(4): 489-503.

Broberg et al.; "Quantification of diffuse myocardial fibrosis and its association with myocardial dysfunction in congenital heart disease", Circulation Cardiovascular Imaging, 2010; 3(6): 727-734.

(Continued)

*Primary Examiner* — Mark Remaly
(74) *Attorney, Agent, or Firm* — Mark S. Cohen; Pearl Cohen Zedek Latzer Baratz LLP

(57) ABSTRACT

The invention provides magnetic resonance imaging methods for detecting cardiac diseases including myocardial fibrosis. Specifically, the invention provides a magnetic resonance imaging (MRI) pulse sequence that could be used to perform magnetization transfer (MT) or chemical exchange saturation transfer (CEST) in the heart.

17 Claims, 4 Drawing Sheets

(56) References Cited

OTHER PUBLICATIONS

Falcão-Pires et al; "Diabetes Mellitus Worsens Diastolic Left Ventricular Dysfunction in Aortic Stenosis Through Altered Myocardial Structure and Cardiomyocyte Stiffness", Clinical Perspective, Circulation 2011; 124(10): 1151-1159.

Ferrauto et al.; "In vivo MRI visualization of different cell populations labeled with PARACEST agents", Magnetic Resonance in Medicine, 2012; n/a-n/a.

Gai et al.; "T(1) mapping of the gadolinium-enhanced myocardium: Adjustment for factors affecting interpatient comparison", Magnetic Resonance in Medicine 65:1407-1415 (2011).

Gilad et al.; "Artificial reporter gene providing MRI contrast based on proton exchange", Nat Biotechnol, 2007; 25(2): 217-219.

Gilad et al. "Feasibility of concurrent dual contrast enhancement using CEST contrast agents and superparamagnetic iron oxide particles", Magn Reson Med, 2009; 61(4): 970-974.

Gilad et al.; "MRI reporter genes", J Nucl Med, 2008; 49(12): 1905-1908.

Iles et al.; Evaluation of diffuse myocardial fibrosis in heart failure with cardiac magnetic resonance contrast-enhanced T1 mapping. Journal of the American College of Cardiology 2008; 52(19): 1574-1580.

Jellis et al.; "Assessment of Nonischemic Myocardial Fibrosis", Journal of the American College of Cardiology, 2010; 56(2): 89-97.

Kim et al.; "Relationship of MRI delayed contrast enhancement to irreversible injury, infarct age, and contractile function", Circulation, 1999; 1001992-2002.

Kim et al.; "Analysis of water-macromolecule proton magnetization transfer in articular cartilage", Magnetic Resonance in Medicine, 1993; 29(2): 211-215.

Kramer et al.; "Contractile reserve and contrast uptake pattern by magnetic resonance imaging and functional recovery after reperfused myocardial infarction", JACC, 2000; 36(6): 1835-1840.

Law et al.; "Diabetes-Induced Alterations in the Extracellular Matrix and Their Impact on Myocardial Function", Microscopy and Microanalysis, 2012; 18(01): 22-34.

Ling et al"; Diffuse Ventricular Fibrosis in Atrial Fibrillation: Noninvasive Evaluation and Relationships With Aging and Systolic Dysfunction", Journal of the American College of Cardiology, vol. 60, No. 23, 2012.

Maya et al.; "Diagnostic approaches for diabetic cardiomyopathy and myocardial fibrosis", Journal of Molecular and Cellular Cardiology, 2010; 48(3): 524-529.

Messroghli et al.; "Human Myocardium: Single-Breath-hold MR T1 Mapping with High Spatial Resolution—Reproducibility Study",Radiology, 2006; 238(3): 1004-1012.

Messroghli et al.; "Myocardial T1 mapping: application to patients with acute and chronic myocardial infarction", Magnetic Resonance in Medicine; 58(1): 34-40.

Prinz et al.; "Myocardial Fibrosis Severity on Cardiac Magnetic Resonance Imaging Predicts Sustained Arrhythmic Events in Hypertrophic Cardiomyopathy", Canadian Journal of Cardiology vol. 29, Issue 3, Mar. 2013, pp. 358-363.

Rathod et al.; "Myocardial fibrosis identified by cardiac magnetic resonance late gadolinium enhancement is associated with adverse ventricular mechanics and ventricular tachycardia late after Fontan operation", Journal of the American College of Cardiology, 2010; 55(16): 1721-1728.

Ross et al.; "Serial MRI evaluation of cardiac structure and function in mice after reperfused myocardial infarction", Magnetic Resonance in Medicine 2002; 47(6): 1158-1168.

Sado et al.; "Novel imaging techniques for diffuse myocardial fibrosis", Future Cardiol. (2011) 7(5), 643-650.

Scholz et al.; "Water-Macromolecular Proton Magnetization Transfer in Infarcted Myocardium: A Method to Enhance Magnetic Resonance Image Contrast", Magnetic Resonance in Medicine, 1995; 33(2): 178-184.

Van Heerebeek et al.; "Diastolic Stiffness of the Failing Diabetic Heart", Circulation, 2008; 117(1): 43-51.

Vandervelde et al.; "Increased inflammatory response and neovascularization in reperfused vs. nonreperfused murine myocardial infarction", Cardiovascular Pathology 2006; 15(2): 83-90.

Vandsburger et al.; "Emerging MRI Methods in Translational Cardiovascular Research", Journal of Cardiovascular Translational Research, 2011; 4(4): 477-492.

Vandsburger et al.; "Improved arterial spin labeling after myocardial infarction in mice using cardiac and respiratory gated look-locker imaging with fuzzy C-means clustering", Magnetic Resonance in Medicine 2010; 63(3): 648-657.

Vandsburger et al.; "MRI reporter genes: applications for imaging of cell survival, proliferation, migration and differentiation", NMR Biomed. 2013; 26: 872-884.

Vinogradov et al.; "CEST: From basic principles to applications, challenges and opportunities", Journal of Magnetic Resonance, 2013; 229(0): 155-172.

Wagner et al.; "Effects of time, dose, and inversion time for acute myocardial infarct size measurements based on magnetic resonance imaging-delayed contrast enhancement", Journal of the American College of Cardiology, 2006; 47(10): 2027-2033.

Ward et al.; "A New Class of Contrast Agents for MRI Based on Proton Chemical Exchange Dependent Saturation Transfer (CEST)", J Magn Reson, 2000; 143(1): 79-87.

Weiss et al; "Stunned, Infarcted, and Normal Myocardium in Dogs: Simultaneous Differentiation by Using Gadolinium-enhanced Cine MR Imaging with Magnetization Transfer Contrast1", Radiology, 2003; 226(3): 723-730.

Wu et al.; "Late gadolinium enhancement by cardiovascular magnetic resonance heralds an adverse prognosis in nonischemic cardiomyopathy", Journal of the American College of Cardiology 2008; 51(25): 2414-2421.

MAGNETIC RESONANCE IMAGING FOR DETECTING CARDIAC DISEASES

CROSS-REFERENCE TO RELATED APPLICATIONS

This application claims priority to and the benefit of U.S. Provisional Patent Application 61/807,791, filed Apr. 13, 2013, which is incorporated by reference herein in its entirety.

GOVERNMENT INTEREST STATEMENT

This invention was made with government support under Contract Number CA 075334, awarded by the National Institutes of Health. The government has certain rights in the invention.

FIELD OF THE INVENTION

The invention relates to magnetic resonance imaging methods for detecting cardiac diseases including myocardial fibrosis. Specifically, the invention relates to a magnetic resonance imaging (MRI) pulse sequence that could be used to perform magnetization transfer (MT) or chemical exchange saturation transfer (CEST) imaging in the heart.

BACKGROUND OF THE INVENTION

Myocardial fibrosis is increasingly associated with arrhythmia, contractile dysfunction, and ventricular remodeling, significantly increasing the risk of sudden cardiac death. Hypertension and diabetes trigger fibrotic processes in the heart, placing a high percentage of the American populace at risk, yet the study of fibrosis and early identification of fibrotic development in high-risk patients is hindered by inadequate fibrosis imaging methods.

Magnetic resonance imaging (MRI) of the heart has emerged as a powerful method by which to identify the presence of dense fibrotic tissue following intravenous (IV) infusion of the contrast agent gadolinium with a delayed contrast enhanced (DCE)-MRI approach. However, myocardial fibrosis can be spatially variable at low densities (termed diffuse fibrosis), or spatially focalized at high densities (termed dense fibrosis), often transitioning from diffuse to dense states as part of disease progression. The sensitivity of DCE-MRI limits detection to dense fibrosis, at which point the 2-year event free survival rate of patients is approximately 50%. Additionally, DCE-MRI techniques face significant limitations in that a large portion of the target patient population is excluded from receiving the required administration of gadolinium-DTPA, and that scan times are lengthy.

The ability to identify the emergence of fibrosis during earlier diseases stages would open a large window for potential therapeutic intervention, as well as create a platform by which to study fibrosis non-invasively and to design targeted therapies. Accordingly, there exists a need to develop an improved MRI methods and systems for myocardial fibrosis and other diseases.

SUMMARY OF THE INVENTION

In one embodiment, the invention provides a cardiac imaging method based on magnetic resonance data, the method comprising: selecting a magnetic resonance parameter to characterize a component in a cardiac tissue of a subject, said magnetic resonance parameter comprising magnetization transfer (MT) or chemical exchange saturation transfer (CEST); providing a pulse sequence to quantify said selected magnetic resonance parameter; acquiring a plurality of sets of signals from said component in said cardiac tissue of said subject; quantifying the acquired signals, wherein said pulse sequence employs a saturation module prior to a constant repetition time (TR) gradient echo readout module in order to encode MT/CEST effect into the steady state longitudinal magnetization within the readout module. In one example, said component is collagen and said saturation module saturates the magnetization of collagen and allows magnetization transfer with surrounding water.

In another embodiment, the invention provides a method for diagnosing, detecting, or monitoring a myocardial fibrosis based on a magnetic resonance imaging of a cardiac tissue, the method comprising: selecting a magnetic resonance parameter to characterize a component in said cardiac tissue, said magnetic resonance parameter comprising magnetization transfer (MT) or chemical exchange saturation transfer (CEST); providing a pulse sequence to quantify said selected magnetic resonance parameter; acquiring a plurality of sets of signals from said component in said cardiac tissue; quantifying the acquired signals, wherein said pulse sequence employs a saturation module prior to a constant repetition time (TR) gradient echo readout module in order to encode MT/CEST effect into the steady state longitudinal magnetization within the readout module.

In another embodiment, the invention provides a method for monitoring the efficacy of a treatment of a myocardial fibrosis, the method comprising an imaging method comprising: selecting a magnetic resonance parameter to characterize a component in said cardiac tissue, said magnetic resonance parameter comprising magnetization transfer (MT) or chemical exchange saturation transfer (CEST); providing a pulse sequence to quantify said selected magnetic resonance parameter; acquiring a plurality of sets of signals from said component in said cardiac tissue; quantifying the acquired signals, wherein said pulse sequence employs a saturation module prior to a constant repetition time (TR) gradient echo readout module in order to encode MT/CEST effect into the steady state longitudinal magnetization within the readout module. In another embodiment, the invention provides a method for treating a myocardial fibrosis, the method comprising the imaging or diagnosis method described herein.

In another embodiment, the invention provides a magnetic imaging system, the system comprising: a unit for selecting a magnetic resonance parameter to characterize a component in a cardiac tissue of a subject, said magnetic resonance parameter comprising magnetization transfer (MT) or chemical exchange saturation transfer (CEST); a unit for providing a pulse sequence to quantify said selected magnetic resonance parameter; a unit for acquiring a plurality of sets of signals from said component in said cardiac tissue of said subject; a unit for quantifying the acquired signals, wherein said pulse sequence employs a saturation module prior to a constant repetition time (TR) gradient echo readout module in order to encode MT/CEST effect into the steady state longitudinal magnetization within the readout module.

Other features and advantages of the present invention will become apparent from the following detailed description examples and figures. It should be understood, however, that the detailed description and the specific examples while indicating preferred embodiments of the invention are given

DETAILED DESCRIPTION OF THE INVENTION

Figure 1:
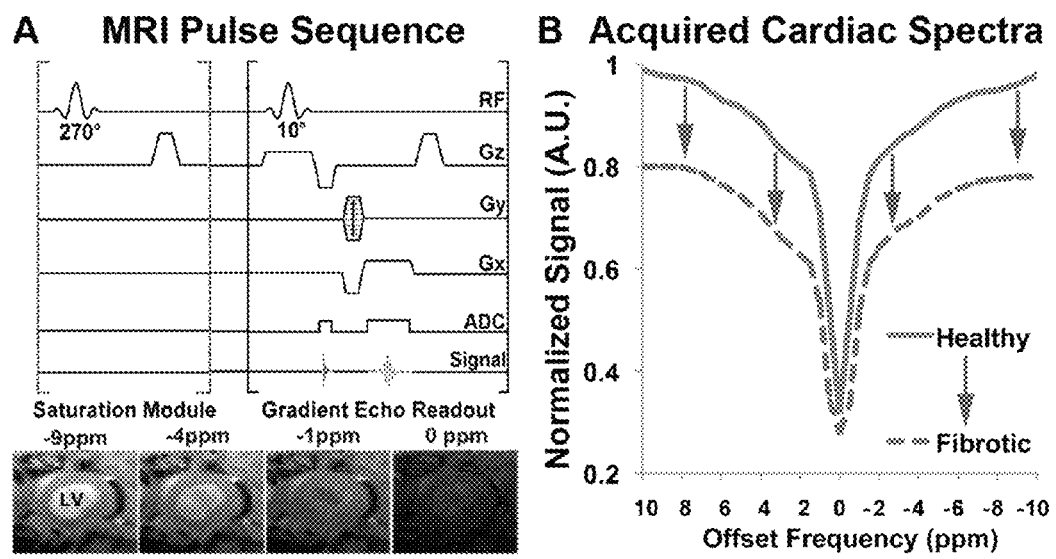
FIG. 1. Methodology and theory of MT/ST-encoded steady state cardiac imaging. (A) Pulse sequence diagram for the MT/ST-encoded steady state cardiac imaging sequence (top). The offset frequency of the saturation pulse within the Saturation Module can be adjusted for each scan. Within an individual scan, the Saturation Module is repeated 28 times for a total of 540 ms, the Gradient Echo Readout is repeated over 1000 ms, and the pairing of the two modules is repeated 128 times. (Bottom) representative images acquired in the healthy mouse heart reveal increased direct saturation as the offset of the saturation module is shifted towards the resonant frequency of water. (B) In the case of fibrotic tissue in the heart, the presence of collagen results in increased MT-generated loss of steady state magnetization, also when the saturation is applied off resonance from the water frequency. Subsequently, the Z-spectrum of fibrotic tissue (red) appears attenuated as compared to normal healthy tissue (blue). In the case of CEST-encoding, the Z-spectrum deviates from normal only about the resonant frequency of the CEST agent.

The invention provides magnetic resonance methods for detecting myocardial fibrosis and other diseases. Specifically, the invention provides a magnetic resonance imaging (MRI) pulse sequence that could be used to perform magnetization transfer (MT) or chemical exchange saturation transfer (CEST).

In one embodiment, provided herein is a cardiac imaging method based on magnetic resonance data, the method comprising: selecting a magnetic resonance parameter to characterize a component in a cardiac tissue of a subject, said magnetic resonance parameter comprising magnetization transfer (MT) or chemical exchange saturation transfer (CEST); providing a pulse sequence to quantify said selected magnetic resonance parameter; acquiring a plurality of sets of signals from said component in said cardiac tissue of said subject; quantifying the acquired signals, wherein said pulse sequence employs a saturation module prior to a constant repetition time (TR) gradient echo readout module in order to encode MT/CEST effect into the steady state longitudinal magnetization within the readout module. In one example, said component is collagen and said saturation module saturates the magnetization of collagen and allows magnetization transfer with surrounding water.

In another embodiment, provided herein is a method for diagnosing, detecting, or monitoring a myocardial fibrosis based on a magnetic resonance imaging of a cardiac tissue, the method comprising: selecting a magnetic resonance parameter to characterize a component in said cardiac tissue, said magnetic resonance parameter comprising magnetization transfer (MT) or chemical exchange saturation transfer (CEST); providing a pulse sequence to quantify said selected magnetic resonance parameter; acquiring a plurality of sets of signals from said component in said cardiac tissue; quantifying the acquired signals, wherein said pulse sequence employs a saturation module prior to a constant repetition time (TR) gradient echo readout module in order to encode MT/CEST effect into the steady state longitudinal magnetization within the readout module. In another embodiment, provided herein is a method for monitoring the efficacy of a treatment of a myocardial fibrosis, the method comprising an imaging method comprising: selecting a magnetic resonance parameter to characterize a component in said cardiac tissue, said magnetic resonance parameter comprising magnetization transfer (MT) or chemical exchange saturation transfer (CEST); providing a pulse sequence to quantify said selected magnetic resonance parameter; acquiring a plurality of sets of signals from said component in said cardiac tissue; quantifying the acquired signals, wherein said pulse sequence employs a saturation module prior to a constant repetition time (TR) gradient echo readout module in order to encode MT/CEST effect into the steady state longitudinal magnetization within the readout module. In another embodiment, provided herein is a method for treating a myocardial fibrosis, the method comprising the imaging or diagnosis method described herein.

Surprisingly, in one embodiment, a fibrotic scar is effectively imaged by an MRI pulse sequence without the use of any contrast agent. The MRI pulse sequence of the present invention can be used to perform magnetization transfer (MT) or chemical exchange saturation transfer (CEST) cardiac MRI. The same method can also be used for detection of targeted CEST agents for cardiac molecular imaging. The physical basis for the sequence is the use of a saturation preparation module that selectively saturates magnetization at specific frequency offsets from water. During this period, saturated magnetization of H protons exchanges with those in surrounding bulk water, such that at the conclusion of the saturation module, the MT/CEST effect is encoded into the steady state longitudinal magnetization (and thus signal intensity) of the MR image.

The concepts of magnetic resonance imaging are well known in the art and fully described in patent application publications, for example, in US 20040059213 and US 20020188190, both of which are incorporated by reference in their entirety.

It is well known that the protons within living tissues have an inherent magnetic moment and spin randomly giving rise to no net magnetization or direction. When a biological sample is placed within the magnetic field of the magnetic resonance scanner, the protons continue to spin but align themselves parallel or antiparallel to the direction of the field ($B_0$) corresponding to low and high energy states respectively. During the course of a magnetic resonance examination, a radiofrequency (RF) pulse ($B_1$) is applied to the sample from a transmitter coil orientated perpendicular to $B_0$ and the protons are momentarily tilted out of alignment; the precession of the induced net transverse magnetization around the axis of the static $B_0$ field produces a voltage across the ends of the receiver coil which is detected as the MR signal. Any variation in the environment of water protons within a fibrotic tissue will lead to altered rates of relaxation of the induced MR signal. The MR parameters that give rise to this altered contrast can be expressed as a quantitative value.

Magnetization transfer (MT), as used herein, refers to the transfer of longitudinal magnetization from the hydrogen nuclei of water that has restricted motion to the hydrogen nuclei of water that moves with many degrees of freedom. The water with restricted motion is generally conceived as being bound to macromolecules through a series of hydrogen bonds. The free water pool is the bulk water of the cytosol.

By saturating the magnetization of a tissue component for example, collagen, and allowing for adequate exchange with water, the spectra of fibrotic tissue acquired using the method of invention can encode a steady longitudinal magnetization of the constant repetition time gradient echo readout scheme In one embodiment, one or more cardiac tissues or the whole heart within in a patient is subjected to the magnetic resonance imaging of the invention. In another embodiment, a biological sample obtained or isolated for a patient is subjected to the magnetic resonance imaging of the invention. Any suitable specimen or sample type known to one of skilled in the art can be used.

In one embodiment, a magnetic resonance parameter comprising magnetization transfer (MT) or chemical exchange saturation transfer (CEST) is selected. A pulse sequence to quantify the selected magnetic resonance parameter is provided. In one embodiment, the pulse sequence employs a saturation module prior to a constant repetition time (TR) gradient echo readout module in order to encode MT/CEST effect into the steady state longitudinal magnetization within the readout module. In some embodiments, saturation module saturates the magnetization of a component, for example, collagen and allows magnetization transfer with surrounding water. A plurality of sets of signals from the component in the cardiac tissue can be obtained and quantified.

In one embodiment, a Z-spectra can be obtained. Also, a reference scan can be obtained for a signal normalization.

A fibrotic tissue spectrum can be obtained and correlated with a healthy tissue spectrum. In some embodiments, the fibrotic tissue spectrum is characterized as the convolution of the normal spectrum with a distribution function, for example, a Lorentzian distribution function (I(f)).

An image can be constructed based on the quantified data of the acquired signals.

In one embodiment, a two-dimensional image can be constructed. In another embodiment, a three-dimensional image can be constructed. The three-dimensional maps of fibrotic geometry can be used for surgical planning of a therapy, for example, a radiofrequency ablation therapy. In addition, measurement of fibrotic geometry can also be used for implantation of cardiac assist devices, as well as improved placement.

In some embodiments, the invention is used to detect a CEST agent or reporter. A cardiac-CEST MRI is a useful tool for monitoring the viability of transplanted CEST reporter gene expressing cells in regenerative cell therapies. Further, with the implementation of multiple CEST reporter genes, complex signaling pathways in cardiac regeneration therapies is investigated simultaneously, serially, and entirely in vivo with non-invasive imaging.

Individual methods of the invention include methods of data acquisition that is performed using any MRI imaging systems (e.g., Phillips, GE and Siemens), known to one of skilled in the art. Data may be acquired using 1.5 T and 3 T systems or greater field strengths. Methods include the use of anatomical MRI of the whole heart or of specific heart regions or fibrotic tissues.

In one embodiment, raw data is transferred from the clinical imaging system to a processing server and reading of data may be performed with a variety of techniques including reading of data on server. Data processing and analysis may include the steps known to one of skilled in the art.

Quality control steps may be included which take into account signal to noise measures in specific locations, line width criteria and the anatomical location of single voxels or multi-voxel slices.

In one embodiment, the method of the invention include data display and reporting including heart areas. Reporting include values for the whole heart or standard regions or fibrotic tissues with reference ranges and error bounds. Reporting may also be for volume corrected or longitudinal results. The reporting may be numerical, graphical or heat-maps of results superimposed on anatomical MRI images. Reporting metrics may be for any measurement individually or for any combination of parameters. Reporting also provide some interpretation of the results including a diagnosis or comparison to a standard, control, or reference population.

In one embodiment, contrast agent is not required in the invention. However, in some embodiment, suitable contrast agents known to one of skilled in the art can be used.

In one embodiment, the invention provides a software package that implements one or more steps in the method including data acquisition from the imaging system, processing of raw data, quality control, calculation of results including combining results from multiple methods, reporting and display of results and provision of an interpretation. In some cases, this software package takes the form of a kit which is implemented by a user of the technique.

In one embodiment, provided herein is a magnetic imaging system, the system comprising: a unit for selecting a magnetic resonance parameter to characterize a component in a cardiac tissue of a subject, said magnetic resonance parameter comprising magnetization transfer (MT) or chemical exchange saturation transfer (CEST); a unit for providing a pulse sequence to quantify said selected magnetic resonance parameter; a unit for acquiring a plurality of sets of signals from said cardiac tissue of said subject; a unit for quantifying the acquired signals, wherein said pulse sequence employs a saturation module prior to a constant repetition time (TR) gradient echo readout module in order to encode MT/CEST effect into the steady state longitudinal magnetization within the readout module.

For the purposes of this description the term "diagnosis" or "diagnosis and monitoring" is used to encompass numerous clinical uses of the invention for management of patients with cardiac or other diseases, including myocardial fibrosis. For example, the invention may be used to diagnose the presence of disease for the first time, to risk stratify patients with a diagnosis of disease into higher and lower risk groups, prediction of disease activity, flares or clinical progression, predicting response to a therapy prior to administration of a drug or after administration of a drug, selection of a specific therapy, selecting a patient for a clinical trial of a new therapy, surgical planning, or using the invention as an endpoint in a clinical trial of a therapeutic. As used herein, the terms "treating" and "treatment" refer to therapeutic treatment, wherein the object is to prevent or slow down (lessen) an undesired physiological change associated with a disease or disorder. Beneficial or desired clinical results include alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder. "Treating" or "treatment" can also mean prolonging survival as compared to expected survival if not receiving treatment. Those in need of treatment include those already with the disease or disorder as well as those prone to having the disease or disorder.

The invention can be applied to any fibrotic disease, including for example, but not limited to, cardiac fibrosis such as myocardial fibrosis. Specifically, the invention is useful for patient with possible or confirmed myocardial fibrosis. In one embodiment, myocardial fibrosis is a diffuse myocardial fibrosis. In another embodiment, myocardial fibrosis is a dense myocardial fibrosis. In yet another embodiment, myocardial fibrosis is associated with myocardial infarction.

The term "subject," as used herein may refer to any human or non-human subjects. The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

Any patent or patent application publication cited herein is incorporated by reference herein in its entirety.

The following examples are presented in order to more fully illustrate the preferred embodiments of the invention. They should in no way be construed, however, as limiting the broad scope of the invention.

EXAMPLES

Example 1

Quantitative Magnetization Transfer Contrast MRI of Tissue Fibrosis

In this work, the inventors of the instant application applied the MT/CEST encoded steady state cardiac imaging method to in vivo MT-mediated monitoring of fibrotic scar formation following myocardial infarction (MI) in the mouse heart. Further applications of these techniques are myriad and expanded upon in further detail below.

Methods

Pulse Sequence Development

The pulse sequence diagram for the MT/CEST encoded steady state cardiac imaging sequence is shown in FIG. 1A. This sequence employs a saturation module (Gaussian, flip angle=270°, bandwidth=200 Hz, duration=13.7 ms, number of pulses=28) prior to a constant TR gradient echo readout module (TR/TE=10.2/3.5 ms, flip angle=10°, number of acquisitions=100) in order to encode the MT/CEST effect into the steady state longitudinal magnetization within the readout module. The total number of sequence repetitions (saturation and readout modules) was 128. Importantly, saturation and readout module parameters were optimized to ensure maximal encoding of MT/CEST contrast with minimal direct saturation of water. Other specific parameters were FOV=2.56×2.56 cm, Matrix=256×128, slices=1, and slice thickness=1 mm. Image reconstruction was accomplished using the Bruker IntraGate system to retrospectively filter out respiratory motion and sort k-space data based on cardiac phase. Sample end-diastolic images of the mouse heart acquired with varying saturation module offsets are shown in FIG. 1A.

Imaging Fibrosis Using MT-Encoded Steady State Cardiac Imaging

Briefly, a saturation pulse train module with offset frequencies of −12, −9, −6, −4, −2, −1, 0, 1, 2, 4, 6, 9, 12 ppm were used in order to obtain Z-spectra, and a separate reference scan (offset=−12 ppm and saturation flip angle=1°) was acquired for signal normalization. Sequence parameters were optimized such that minimal direct saturation of water magnetization occurred at frequencies far from 0 ppm, as seen in the healthy spectrum in FIG. 1B. In contrast to water, which demonstrates selective saturation across a narrow bandwidth, collagen demonstrates saturation across a relatively broad bandwidth. By saturating the magnetization of collagen and allowing for adequate exchange with water, spectra of fibrotic tissue acquired using the method detailed above demonstrate depressed steady state signal (FIG. 1B, red spectrum) when compared to normal spectra.

Figure 2:
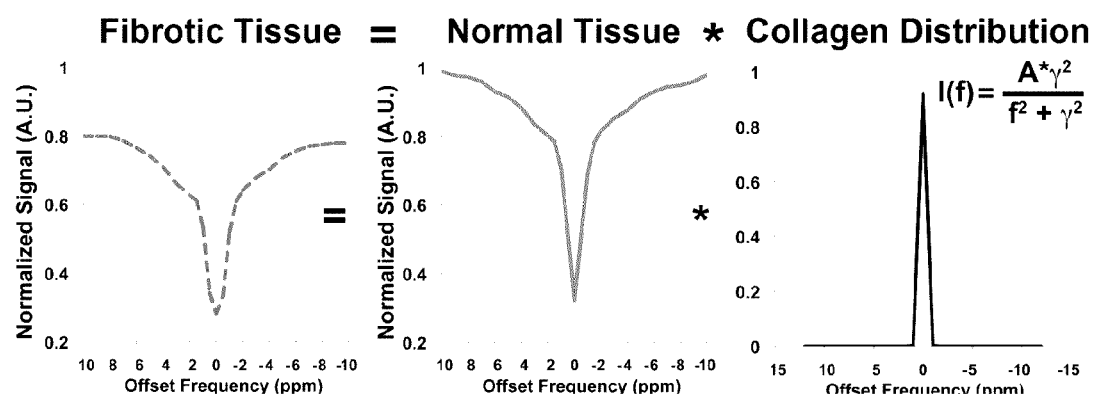
FIG. 2. Modeling the impact of fibrosis on steady state longitudinal magnetization. The contribution of fibrotic tissue to the Z-spectrum can be characterized as the convolution of the normal tissue spectrum with a Lorentzian distribution function I(f) that describes the presence of and relative MT effect of collagen.

The relationship between the fibrotic tissue spectrum and that of healthy tissue was characterized mathematically as the convolution of the normal spectrum with a Lorentzian distribution function (I(f)) describing the MT-effects of collagen as shown in FIG. 2. Within I(f), the variables A and γ describe the steady state magnetization and line broadening effects of fibrosis, respectively. Normalized spectra were obtained by dividing the signal intensity within the myocardium by the corresponding reference scan signal intensity. The values of A and γ were optimized via RMS minimization, and from this the fibrotic score was calculated for a given region of interest (ROI) as F.S.=$(1/A_{ROI}-1)*100$.

Animal Experiments for Fibrosis Imaging

All imaging was performed on a 9.4 T Bruker Biospec (Ettlingen, Germany) scanner using a cylindrical volume coil for excitation and a single element surface coil for reception. Mice were anesthetized using 1.25% isoflurane in oxygen, and heated using thermostated circulating water. MI was surgically induced via permanent ligation of the left anterior descending (LAD) coronary artery in C57B6 male mice (n=7) at 8 weeks of age. Mice were imaged using the previously described sequence at 1, 7, 10, 14 and 21 days after MI. At the conclusion of MT-cardiac imaging, delayed contrast enhanced (DCE) images were acquired following intraperitoneal (IP) injection of gadolinium-DTPA (0.1 mmol/kg body weight) via an indwelling IP catheter. T1-weighted DCE images were acquired using a cine imaging sequence with identical spatial parameters and flip angle=25°. Image analysis was performed on end diastolic images by defining infarct (hyper-intense), border (5 pixels away from infarct zone circumferentially), and remote (remainder) myocardial zones based on signal enhancement of DCE images. At the conclusion of imaging at 21 days after MI, hearts were isolated, fixed, sectioned, and stained for collagen using Masson's Trichrome staining.

Results

Imaging Fibrosis Using MT-Encoded Steady State Cardiac Imaging

Figure 3:
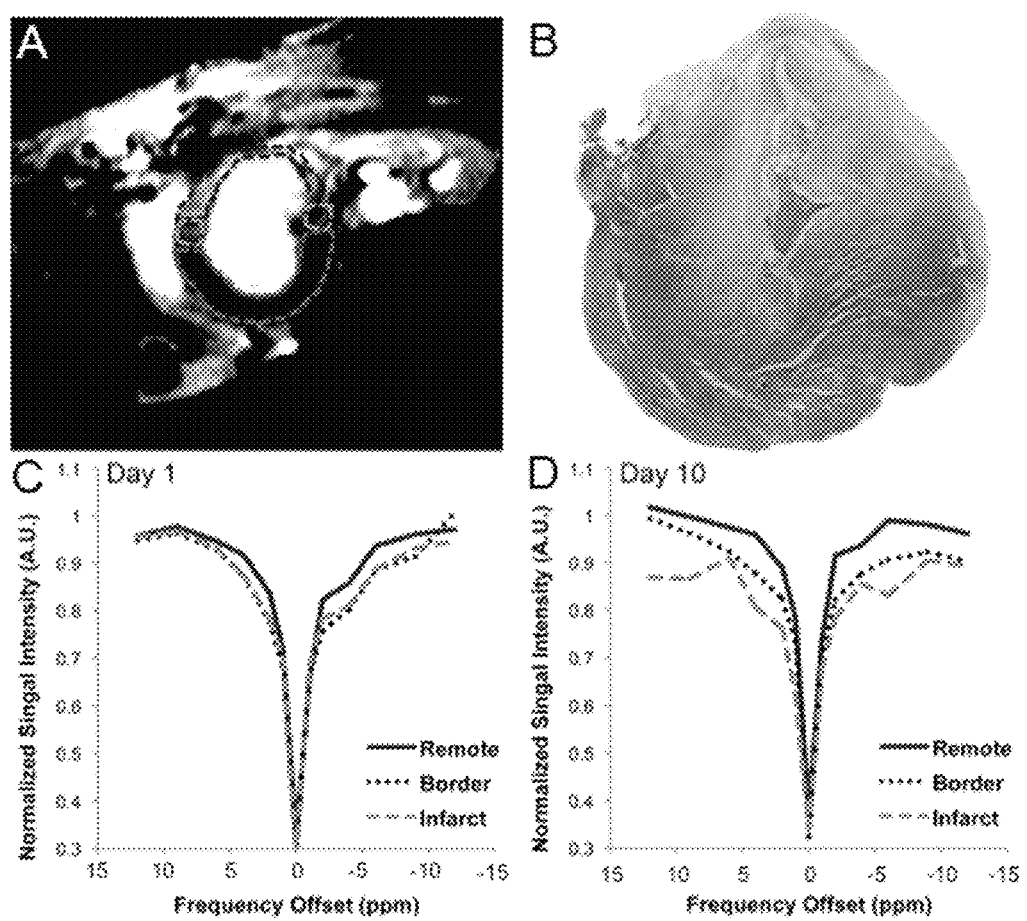
FIG. 3. MT-encoded imaging of fibrotic development after MI in mice. (A) Delayed contrast enhanced MR was used to define infarct (blue dotted line), and remote (red dotted line) myocardium based on signal enhancement patterns following administration of gadolinium-DTPA. The border zone (orange dotted line) was defined as five pixels away from the infarct zone along the circumferential direction. (B) Masson's Trichrome staining of isolated cardiac tissue sections from hearts removed 21 days after MI reveal the spatial distribution of collagen within the imaging slice. (C) Spectra from the three zones acquired 1 day after MI demonstrate limited MT and line broadening effects, likely from edema. (D) By 10 days after MI, significant deposition of collagenous scar tissue within the infarct zone results in a pronounced MT effect visible within the infarct zone spectrum. An intermediate effect is seen in the border zone tissue, in which a mixed population of collagen and surviving cardiac tissue is present.
Figure 4:
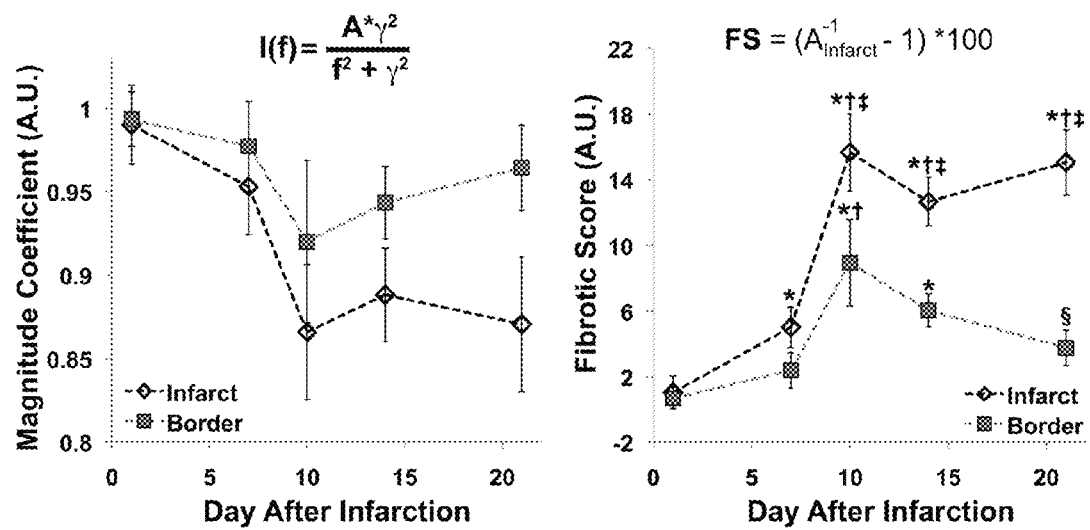
FIG. 4. Time-course of changes in regional collagen characterization after MI. The magnitude coefficient (A) within the Lorentzian characterization function I(f) decreased in both infarct and border zone myocardium at 10 days after MI (left) reflecting the deposition of collagen during scar formation. The fibrotic score (right) reveals significant increase in both infarct and border zone myocardium. Within infarct zone myocardium, both A and fibrotic score remain relatively unchanged after 10 days post-MI. In contrast, both A and fibrotic score decrease between 10 and 21 days in border zone myocardium (*$P<0.05$ vs. Day 1, †$P<0.05$ vs. Day 7, ‡$P<0.05$ vs. Border, §$P<0.05$ vs. Day 10).

MT-encoded steady state cardiac imaging revealed similar spectral behavior in remote, border, and infarct zone myocardium immediately after MI (FIG. 3). By 10 days after MI, the spectra of infarct zone myocardium diverged significantly from those of remote zone myocardium (FIG. 3). Border zone spectra typically demonstrated an intermediate MT effect. Masson's trichrome staining of isolated tissue sections confirmed significant collagen deposition in infarct zone myocardium, with mixed collagen in border zone myocardium (FIG. 3). The time-course of change in the magnitude coefficient (A) of the Lorentzian distribution function I(f), and corresponding changes in fibrotic score (F.S.) revealed rapid development of collagenous scar tissue in the infarct zone between days 7-10 (FIG. 4), with limited development thereafter. In border zone myocardium, an increase in fibrotic tissue content appears between days 7-10 after MI. The apparent reversal of fibrotic development within border zone tissue likely reflects further scar maturation and extension from the infarct zone, thus redefining the spatial localization of the border zone over time.

The development of MT/CEST encoded steady state cardiac imaging represents a novel advancement in cardiac molecular MRI, enabling MT/CEST imaging in the heart for the first time. This new method enables measurement of cardiac fibrosis without the use of exogenous contrast agents, and would also enable use of molecular CEST contrast agents in the beating heart. The potential applications of this technique range from broad novel diagnostic purposes, to surgical planning, to molecular imaging in regenerative medicine.

The presence of collagen induced MT-effects has generally been viewed as either a source of artifact in MR images, or as a mechanism by which to selectively visualize scar tissue based on selective saturation of water magnetization. In tissue containing a large collagen component, the excitation of collagen magnetization via tailored RF pulses, and subsequent MT with surrounding water, leads to a loss of signal. In the work discussed above, MT was constructively utilized to encode the presence of collagen into the signal intensity of acquired MR images. Modeling the encoded MT-effect within acquired cardiac spectra to measure fibrotic score enabled measurement of the development of collagenous scar tissue during the time-course of infarct healing, in close agreement with that demonstrated via histological techniques. Established MRI methods to identify fibrotic scar tissue require visual identification of signal enhancement on T1-weighted images following intravenous administration of chelated gadolinium salts. In contrast to these techniques, the invention uses an entirely endogenous contrast mechanism, which is significantly less invasive, and provides a stronger quantitative component.

In addition to the immense importance of detection of the endogenous collagen contrast in the heart, the MRI pulse sequence reported here enables cardiac imaging of CEST based contrast media. CEST-MRI is emerging as a powerful technique by which to selectively visualize MRI reporter genes as well as a unique class of exogenously delivered contrast agents. To date, CEST-MRI has been performed in stationary tissues such as the brain, breast, and tumors, but never in the heart. Conventional CEST acquisition strategies employ a CEST-encoding preparation module (similar to that used in this study), followed by a fast spin-echo readout mechanism. However, due to constant movement during contraction, the use of spin-echo readout schemes is not suitable for cardiac-CEST imaging. Cardiac imaging is commonly performed using constant repetition time gradient echo acquisitions with retrospective reconstruction algorithms. Our method encodes the CEST-preparation into the steady state longitudinal magnetization of the constant repetition time gradient echo readout scheme, and was optimized to maximize the CEST signature whilst minimizing direct saturation of water magnetization. The exact timing for the saturation and readout modules was chosen based on knowledge of the mean residence time of capillary blood water, and concerns of T1-relaxation in the myocardium.

In the current study the inventors demonstrated applications of MT/CEST-encoded cardiac imaging. Importantly, the applications of these techniques span far beyond that which was demonstrated in the study described above. For example, in vivo measurement of myocardial fibrosis has been performed using DCE-MRI with a T1-mapping approach. Such techniques face significant limitations in that a large portion of the target patient population is excluded from receiving the required administration of gadolinium-DTPA, and that scan times are lengthy. In contrast, quantitative fibrosis mapping using the technique outlined in this study would enable a rapid and endogenous mechanism by which to measure myocardial fibrosis in patients. This capability has broad application to the study of fibrotic development in pre-clinical models, to diagnose fibrotic development earlier in patients, and to assess the efficacy of anti-fibrotic therapies during development and treatment. In addition, this could be used to create three-dimensional maps of fibrotic geometry for surgical planning of radiofrequency ablation therapy, as described above. Further, as described above, measurement of fibrotic geometry could lead to refined criteria for implantation of cardiac assist devices, as well as improved placement. Separately, as described above, cardiac-CEST MRI can become a useful tool for monitoring the viability of transplanted CEST reporter gene expressing cells in regenerative cell therapies. Further, with the implementation of multiple CEST reporter genes, complex signaling pathways in cardiac regeneration therapies could be investigated simultaneously, serially, and entirely in vivo with non-invasive imaging.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A cardiac imaging method based on magnetic resonance data, said method comprising:
    selecting a magnetic resonance parameter to characterize a component in a cardiac tissue of a subject, said magnetic resonance parameter comprising magnetization transfer (MT) or chemical exchange saturation transfer (CEST);
providing a pulse sequence to quantify said selected magnetic resonance parameter;
acquiring a plurality of sets of signals from said component in said cardiac tissue of said subject;
quantifying the acquired signals,
wherein said pulse sequence employs a saturation module prior to a constant repetition time (TR) gradient echo readout module in order to encode MT or CEST effect into the steady state longitudinal magnetization within the readout module.

2. The method of claim 1, said component in said cardiac tissue is a collagen.

3. The method of claim 2, wherein said saturation module saturates the magnetization of collagen and allows magnetization transfer with surrounding water.

4. The method of claim 1, further comprising obtaining Z-spectra.

5. The method of claim 1, further comprising Obtaining a reference scan for a signal normalization.

6. The method of claim 1, further comprising correlating a fibrotic tissue spectrum with a healthy tissue spectrum.

7. The method of claim 6, further comprising characterizing the fibrotic tissue spectrum as the convolution of the normal spectrum with a Lorentzian distribution function (I(f).

8. The method of claim 1, further comprising detecting a CEST agent or reporter.

9. The method of claim 1, further comprising constructing an image based on the quantified data of the acquired signals.

10. A method for diagnosing, detecting, or monitoring a myocardial fibrosis based on a magnetic resonance imaging of a cardiac tissue, said method comprising:
selecting a magnetic resonance parameter to characterize a component in said cardiac tissue, said magnetic resonance parameter comprising magnetization transfer (MT) or chemical exchange saturation transfer (CEST);
providing a pulse sequence to quantify said selected magnetic resonance parameter;
acquiring a plurality of sets of signals from said component in said cardiac tissue;
quantifying the acquired signals,
wherein said pulse sequence employs a saturation module prior to a constant repetition time (TR) gradient echo readout module in order to encode MT or CEST effect into the steady state longitudinal magnetization within the readout module.

11. The method of claim 10, wherein said myocardial fibrosis is associated with myocardial infarction.

12. The method of claim 10, wherein said myocardial fibrosis is a diffuse myocardial fibrosis.

13. The method of claim 10, wherein said myocardial fibrosis is a dense myocardial fibrosis.

14. A method for treating a myocardial fibrosis, the method comprising the method of claim 1.

15. A method for assessing the efficacy of an anti-fibrotic therapy, said method comprising:
selecting a magnetic resonance parameter to characterize a component in a cardiac tissue of a subject, said magnetic resonance parameter comprising magnetization transfer (MT) or chemical exchange saturation transfer (CEST);
providing a pulse sequence to quantify said selected magnetic resonance parameter;
acquiring a plurality of sets of signals from said component in said cardiac tissue of said subject;
quantifying the acquired signals,
wherein said pulse sequence employs a saturation module prior to a constant repetition time (TR) gradient echo readout module in order to encode MT or CEST effect into the steady state longitudinal magnetization within the readout module.

16. A surgical method for treating a myocardial fibrosis, said method comprising:
selecting a magnetic resonance parameter to characterize a component in a cardiac tissue of a subject, said magnetic resonance parameter comprising magnetization transfer (MT) or chemical exchange saturation transfer (CEST);
providing a pulse sequence to quantify said selected magnetic resonance parameter;
acquiring a plurality of sets of signals from said component in said cardiac tissue of said subject;
quantifying the acquired signals,
wherein said pulse sequence employs a saturation module prior to a constant repetition time (TR) gradient echo readout module in order to encode MT or CEST effect into the steady state longitudinal magnetization within the readout module.

17. A method for predicting a risk of sudden cardiac death based on a magnetic resonance imaging of a cardiac tissue, the method comprising:
selecting a magnetic resonance parameter to characterize a component in said cardiac tissue, said magnetic resonance parameter comprising magnetization transfer (NIT) or chemical exchange saturation transfer (CEST);
providing a pulse sequence to quantify said selected magnetic resonance parameter;
acquiring a plurality of sets of signals from said component in said cardiac tissue;
quantifying the acquired signals, wherein said pulse sequence employs a saturation module prior to a constant repetition time (TR) gradient echo readout module in order to encode MT or CEST effect into the steady state longitudinal magnetization within the readout module.

* * * * *